United States Patent [19]

Dooley et al.

[11] Patent Number: 5,451,618
[45] Date of Patent: Sep. 19, 1995

[54] PARTIALLY UNSATURATED TRIORGANOTIN COMPOUNDS FOR USE IN BIOCIDAL PAINT

[75] Inventors: Carol A. Dooley; Elek Lindner, both of San Diego, Calif.

[73] Assignee: The United States of America as represented by the Secretary of the Navy, Washington, D.C.

[21] Appl. No.: 175,890

[22] Filed: Dec. 30, 1993

[51] Int. Cl.⁶ .................. C08J 3/00; C08C 19/00
[52] U.S. Cl. .................. 523/122; 523/177; 525/364; 526/240
[58] Field of Search .......... 523/122, 177; 525/364; 526/240

[56] References Cited

U.S. PATENT DOCUMENTS

| | | | |
|---|---|---|---|
| 2,962,522 | 11/1960 | Gibbons, Jr. et al. | 260/429.7 |
| 2,965,661 | 12/1960 | Ramsden | 260/429.7 |
| 3,012,999 | 12/1961 | Evieux | 260/87.5 |
| 3,100,217 | 8/1963 | Bartocha | 260/448 |
| 3,415,857 | 12/1968 | Hoye | 260/429.7 |
| 4,052,354 | 10/1977 | Beiter et al. | 523/122 |
| 4,082,709 | 4/1978 | Dyckman et al. | 260/22 CB |
| 4,098,971 | 7/1978 | Phillip et al. | 526/16 |
| 4,130,432 | 12/1978 | Wehner et al. | 523/122 |
| 4,262,097 | 4/1981 | Dawans et al. | 525/310 |
| 4,485,197 | 11/1984 | Yokoi et al. | 523/177 |
| 4,532,269 | 7/1985 | Gitlitz et al. | 523/122 |
| 4,554,185 | 11/1985 | Lane et al. | 427/385.5 |
| 4,576,838 | 3/1986 | Rosen et al. | 427/385.5 |
| 4,596,724 | 6/1986 | Lane et al. | 427/385.5 |
| 4,835,231 | 5/1989 | Yamamori et al. | 526/240 |
| 4,914,141 | 4/1990 | Matsuo et al. | 523/122 |
| 4,959,417 | 9/1990 | Miyazono et al. | 525/274 |
| 5,006,554 | 4/1991 | Dooley et al. | 514/493 |
| 5,059,702 | 10/1991 | Dooley et al. | |

OTHER PUBLICATIONS

S. Boue et al, "Organometallic Compounds. VI. Electron Impact Fragmentation of Some Mixed & Symmetrical Tetraalkyltins", Bulletin Societe de Chimie Belge, vol. 77, p. 43, 1968.
S. Boue et al, "Organometallic Compounds. XI. Synthesis & Properties of a Series of Racemic Tetraalkyltins", Bulletin Societe de Chimie Belge, vol. 78, p. 135, 1969.
A. A. Bulich, "A Practical & Reliable Method for Monitoring the Toxicity of Aquatic Samples", Process Biochemistry, Mar./Apr., 1982, p. 45.
A. A. Bulich et al, "Use of the Luminexcent Bacterial System for the Rapid Assessment of Aquatic Toxicity", ISA Transactions, vol. 20, No. 1, p. 29, 1981.
H. C. Clark et al, "Pi-bonding between C≡C Bonds and Tin in Alkenyltin Compounds", Canadian Journal of Chemistry, vol. 48, p. 2670, 1970.
J. C. Cochran et al, "Kinetics of the Protodestannylation of Vinyltrialkyltins & Substituted Vinyltrialkyltins", Organometallics, vol. 1, p. 586, 1982.
A. G. Davies et al, Comprehensive Organomettallic Chemistry, Pergamon Press, New York, pp. 519–627, 1982.
C. A. Dooley, "Synthesis, Stability & Toxicity of Organotin Antifoulant Compounds with Unsaturated Carbon Chains", In IR-IED '90, NOSC TR 1957, vol. 2, p. 13, Naval Ocean Systems Center, San Diego, Calif.
C. A. Dooley et al, "Response of Bioluminexcent Bacteria to Alkyltin Compounds", Oceans 87, vol. 4, p. 1517.

(List continued on next page.)

Primary Examiner—Paul R. Michl
Assistant Examiner—LaVonda R. DeWitt
Attorney, Agent, or Firm—Harvey Fendelman; Thomas Glenn Keough

[57] ABSTRACT

Triorganotin toxicants are disclosed that are made of mixed saturated and unsaturated four-carbon chains with double bonds at C-1 and C-3. Incorporation of these compounds into random 50:50 copolymers of methacrylic acid and methylmethacrylate produces copolymer compositions that may be used as antifouling coatings for ship hulls. Methods for manufacturing the triorganotin toxicants and the copolymer compositions are also disclosed.

20 Claims, 2 Drawing Sheets

OTHER PUBLICATIONS

C. A. Dooley et al, "Synthesis & Mass Spectra of Butenyltin Compounds", *NOSC TR 1272,* Naval Ocean Systems Center, San Diego, Calif., 1989a.

C. A. Dooley et al, "Stability & Microtox Response of Butenyltin Compounds", *Applied Organometallic Chemistry,* vol. 3, p. 171, 1989b.

R. K. Ingham et al, "Organotin Compounds", *Chemical Reviews,* vol. 60, p. 459, 1960.

S. M. O'Brien et al, "Isoleptic Allyl Derivatives of Various Metals", *Inorganic Synthesis,* vol. 13, p. 73, 1971.

S. D. Rosenberg et al, "The Preparation of Some Unsymmetrical Organotin Bromides & Acetates", *Journal of the American Chemical Society,* vol. 81, p. 972, 1959.

S. D. Rosenberg et al, "The Preparation of Some Vinyltin Compounds with Vinylmagnesium Chloride" *Journal of the American Chemical Society,* vol. 79, p. 2137, 1957.

D. Seyferth et al, "Vinyl Derivatives of the Metals. I. Synthesis of Vinyltin Compounds", *Journal of the American Chemical Society,* vol. 79, p. 515, 1957.

M. O. Stallard et al, "Optimization of Butyltin Measurements for Seawater, Tissue, & Marine Sediment Samples", *Applied Organometallic Chemistry,* vol. 3, p. 105, 1989.

A. O. Valkirs et al, "Speciation of Butyltins in Seawater & Marine Sediments by Hydride Derivatives & Atomic Absorption Detection", NOSC TR 1037, Naval Ocean Systems Center, San Diego, Calif., 1985.

K. V. Vijayaraghavan, "Organometallic Compounds of the Allyl Radical. Part II. Tin Tetra Allyl & its Derivatives", *Journal of the Indian Chemical Society,* vol. 22, p. 135, 1945.

PARTIALLY UNSATURATED TRIORGANOTIN COMPOUNDS FOR USE IN BIOCIDAL PAINT

STATEMENT OF GOVERNMENT INTEREST

The invention described herein may be manufactured and used by or for the Government of the United States of America for governmental purposes without the payment of any royalties thereon or therefor.

FIELD OF THE INVENTION

The present invention relates generally to biocidal paints and more particularly to biocidal paints which are environmentally benign.

BACKGROUND OF THE INVENTION

It is desirable in a wide variety of applications to provide paints which contain biocidal agents. For example, as recognized by the present invention, it would be advantageous to provide a biocidal agent in paint which is used to cover bathroom walls, to inhibit the development of fungus on the walls. As another example, and of particular concern to the present invention, is the provision of biocidal paint (often referred to as "antifouling coatings") for ships' hulls.

Tributyltin (often referred to as organotin) biocidal compounds were added to coatings developed in the 1970s to replace copper-based toxicants in marine antifouling coatings. The newest organotin-based marine antifouling coatings contain toxicants which are released from a polymer backbone upon exposure to water. The released toxicants adversely affect the larval forms of marine fouling organisms.

Tributyltin-based coatings have a much longer service life with concomitant savings in fuel and maintenance costs compared with copper-based compounds. Indeed, tributyltin compounds have been found to be very effective biocidal agents.

Unfortunately, the use of tributyltin compounds as antifoulants for ships' hulls is not environmentally as benign as federal and state environmental guidelines require. More particularly, tributyltin compounds persist in the water column and sediments and have the potential for bioaccumulation. In other words, tributyltin compounds tend to be environmentally hazardous as defined by current environmental statutes, because they do not quickly degrade, i.e., they do not quickly break down to less toxic derivatives after fulfilling their biocide function. It will be appreciated that the same environmental considerations apply to other applications, e.g., to bathroom paint applications, wherein water which contacts the paint can retain the toxic compounds and can ultimately be washed off the walls into sewage lines.

As recognized in previous U.S. Pat. No. 5,006,554 for an invention entitled "Organotin Compounds", it is possible to provide an organotin compound which is an effective biocidal agent, and which degrades much faster than tributyltin to a less-toxic species. In the above-mentioned U.S. patent, tributyltin is replaced by tributenyltin, and the tributenyltin has been found to be a very effective biocidal agent which quickly degrades to a less-toxic species. More particularly, tributenyltin is an effective biocide which degrades about an order of magnitude more quickly than tributyltin.

Unfortunately, it has been found that when tributenyltin compounds are esterified to copolymers for antifouling marine paint applications, the resulting polymers are intractable. Stated differently, the insolubility of tributenyltin-based polymers in common organic solvents severely hampers their use as marine antifouling coatings.

SUMMARY OF THE INVENTION

A method for inhibiting the attachment of organisms to a surface includes the steps of administering an effective amount of a toxic substance onto the surface. In accordance with the present invention, the toxic substance includes a substance in the group consisting of dibutyl-1-butenyltin, butyldi-1-butenyltin, dibutyl-3-butenyltin, and butyldi-3-butenyltin. For marine antifouling applications, the method can further include the step of chemically bonding the substance to a polymer backbone.

In another aspect of the present invention, a biocidal substance is disclosed for inhibiting organism growth on a surface, and the substance readily degrades to a non-toxic species. As provided by the present invention, the substance includes at least one triorganotin compound containing a double bond at C-1 or C-3 in either one or two of the three carbon chains. For certain applications, the substance is disposed in a polymeric matrix.

In still another aspect of the present invention, a method is disclosed for inhibiting the growth of organisms on a surface. The method of the present invention includes administering to the surface an effective amount of a substance toxic to the organisms. The toxic substance includes a triorganotin moiety, and the triorganotin moiety has at least one site of unsaturation on one or two of its organic groups. If desired, the triorganotin moiety can be covalently bonded to an organic polymer, preferably a copolymer of methacrylic acid and methylmethacrylate. As intended by the present invention, each of the organic groups of the triorganotin moiety is two (2) to ten (10) carbon atoms in length.

In yet another aspect of the present invention, a triorganotin ester of an alkenylcarboxylic acid is disclosed, wherein the triorganotin group of the ester has a double bond in one or two of its organic groups. Preferably, the ester has the formula $[H_2C=C(CH_3)C(O)O-]SnR_1R_2R_3$, wherein $R_1$, $R_2$ and $R_3$ are organic groups each containing from two (2) to ten (10) carbon atoms.

In another aspect of the present invention, a triorganotin polymer has a plurality of triorganotin groups covalently bonded to an organic polymer backbone, and each of the triorganotin groups has a double bond in one or two of its organic groups.

In still another aspect of the present invention, a method is disclosed for forming a triorganotin polymer which has biocidal activity. The method includes the steps of reacting a bis(triorganotin)oxide compound with an alkenylcarboxylic acid to form a triorganotin-alkenylcarboxylate monomer. Then, the monomer is polymerized to form the triorganotin polymer. Alternatively, the triorganotin compounds can be grafted to an existing polymer or copolymer backbone that contains free carboxylic acid groups.

Accordingly, it is an object of the present invention to provide a biocidal agent which can be incorporated into a paint.

Another object is to provide for paint a biocidal agent which rapidly degrades to less-toxic species in the environment.

Still another object of the present invention is to provide a biocidal agent which is suitable for marine coatings and which rapidly degrades to less-toxic species in the environment.

Yet another object is to provide a biocidal agent for an easy to use paint that is cost-effective to manufacture.

These and other objects of the invention will become more readily apparent to one skilled in the art to which this invention pertains from the ensuing specification and claims when taken in conjunction with the appended drawings.

BRIEF DESCRIPTION OF THE DRAWINGS

The file of this patent includes at least one drawing executed in color.

All formulations containing at least 25% by weight tin-bearing monomer possess good antifouling performance despite the amount of triorganotin which can be found in the seawater to which the coatings have been exposed. Careful sampling of the copolymer surface with an ethanol wash indicates that the bound species is triorganotin. Thus, circumstantial evidence indicates that hydrolysis of the biocide from the copolymer backbone and degradation of the biocide, in the case of B-31 and B-32, are nearly simultaneous.

DESCRIPTION OF THE PREFERRED EMBODIMENT

Figure 1:
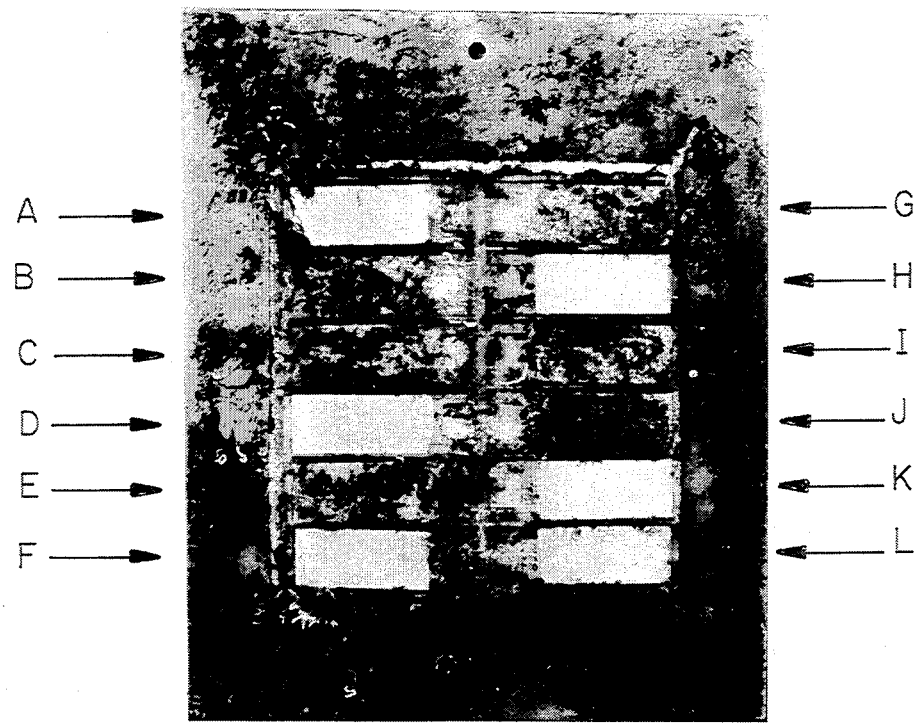
FIG. 1 is a photograph depicting surface areas treated with a known tributyltin biocide B-00 and other surface areas treated with the biocides B-31 and B-32 of the present invention, with all these surface areas appearing to have substantially identical degrees of biologic growth inhibition. Other surface areas coated with other substances are shown to provide substantially no growth inhibition during a control period for comparison purposes.
Figure 2:
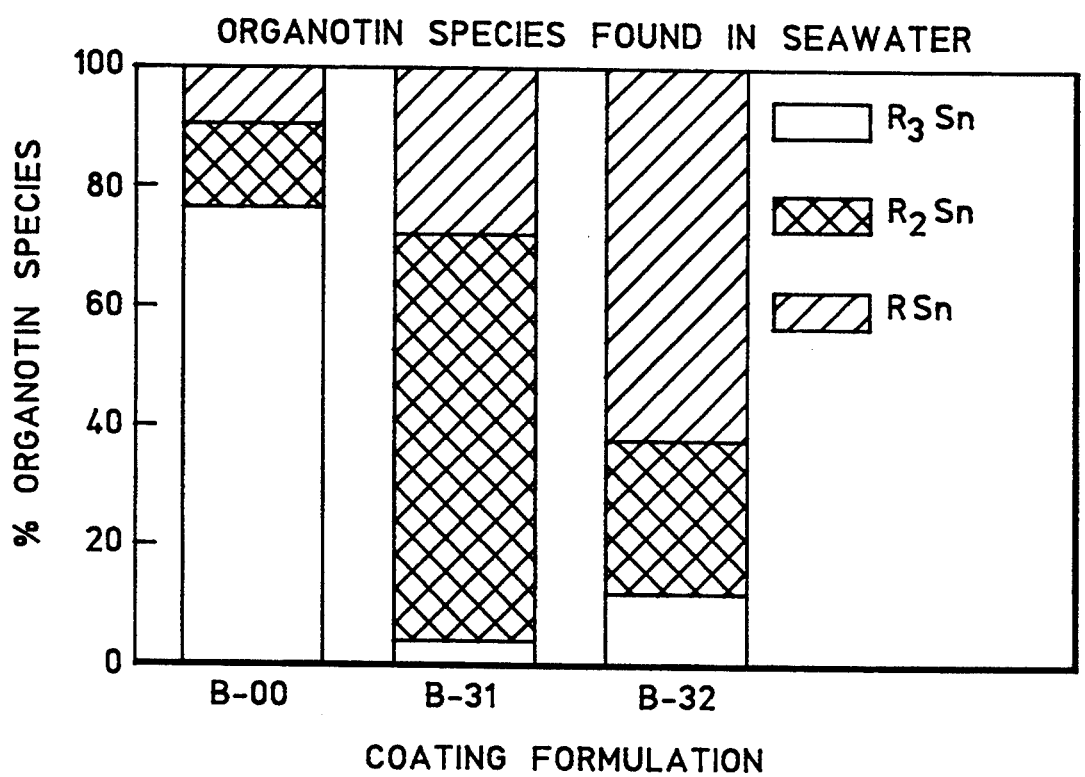
FIG. 2 shows the proportions of organotin species that appear in the seawater when coatings are applied to a surface and exposed to seawater. Primarily the toxic triorganotin species appears when the copolymer containing tributyltin, B-00, is exposed to seawater. In contrast, mainly the low toxicity degradation products, the di- and mono-organotin species, are found in the seawater when the coatings containing B-31 and B-32 are exposed to seawater. Degradation of B-31 and B-32 to the di- and mono-organotin species appears to occur within the first 15 minutes of the hydrolysis of the biocidal triorganotin from the copolymer backbone; i.e. the measurement cannot be made faster than 15 minutes. The carbon chains containing the double bond are preferentially cleaved from the molecule.

The details of the present invention, both as to its structure and operation, can best be understood in reference to the accompanying detailed description and appendices. FIG. 1 shows a surface treated with a known tributyltin biocide B-00 and surfaces treated with the biocides of the present invention B-31 and B-32, with the surfaces appearing to have substantially identical degrees of biologic growth inhibition. FIG. 2 sets forth data that shows that the biocide of the present invention readily degrades to a relatively non-toxic species as compared to tributyltin biocides. More specifically, FIG. 2 sets forth data showing that relatively immediate degradation of the biocide of the present invention occurs upon its release from the coating matrix.

In accordance with the present invention, triorganotin compounds are synthesized which contain at least one double bond in either one or two of the three organic groups of the compounds. Stated differently, dialkylalkenyltin bromide and alkyldialkenyltin bromide are synthesized, with the preferred compound for marine anti-fouling applications being dibutyl-3-butenyltin bromide and butyldi-3-butenyltin bromide. The present invention envisions alkyl and alkenyl groups that have between two (2) and ten (10) carbon atoms each, and preferably have four (4) carbon atoms each, the alkenyl groups having one double bond at C-1 or C-3 in the form of dibutyl-1-butenyltin bromide, butyldi-1-butenyltin bromide, dibutyl-3-butenyltin bromide, and butyldi-3-butenyltin bromide. Bromide is preferred, but the skilled artisan will recognize that other appropriate substances may replace bromide.

Next, the triorganotin compounds are reacted with methacrylic acid (MAA) to form a corresponding ester, and the ester is then polymerized with methylmethacrylate (MMA) to produce 50:50 random copolymers for marine anti-fouling applications. Alternatively, the triorganotin compounds can be grafted to an existing polymer or copolymer backbone that contains free carboxylic acid groups. The triorganotin compounds can alternatively be mixed with ordinary house paint or other paint to establish a rapidly-degradable (and hence environmentally benign) biocidal paint.

First, the following chemicals are obtained. Dibutyltin dichloride, butyltin trichloride, 1-bromo-1-butene, and 2,2-azobis-2-methylpropionitrile are obtained from Pfaltz & Bauer (Waterbury, Conn.). Resublimed magnesium chips and tributyltin chloride are obtained from Alfa Products (Danvers, Mass.). Methylmethacrylate, methacrylic acid and 4-bromo-1-butene are obtained from Aldrich Chemical Company (Milwaukee, Wis.). All of the above-listed substances are used without further purification.

The procedures followed below are undertaken with the following instrumentation and equipment. Retention times and mass spectra of synthesized and purchased compounds are obtained with a Hewlett-Packard Model 5890A Gas Chromatograph directly connected to a Hewlett-Packard Model 5970 Mass Selective Detector (GC/MS). Data collection and reduction is performed with a Hewlett-Packard 9000-300 Computer using Model 59970C ChemStation software. Samples are run using splitless injection onto a 12.5 m by 0.2 mm I.D. HP 1 fused silica capillary column with 0.33 micrometer coating thickness. Helium carrier gas is used at a head pressure of 40 kPa. The oven is programmed, after an initial two-minute hold at 50° C., to 230° C. at 30° C./min. Injector, transfer line and detector are at 250° C. Masses are scanned between 50 and 450 amu. Retention times and relative ion abundances are specific for the compounds of interest.

Infrared spectrometry is used to determine the position of the double bond and to show that double bond position is retained after bromination of the compound, that addition of bromine across the double bond did not occur, and that the double bond is retained in the polymerized product. The C=C vibration band is found at approximately 1600 cm-1 and 1640 cm-1 for the 1-butenyltin and the 3-butenyltin compounds, respectively.

IR spectra are obtained of the neat compounds or polymers using a BioRad FTS-60 Fourier Transform Infrared Spectrometer.

Biocidal compounds are synthesized using the appropriate tetra-compounds which are prepared by first preparing dibutyldi-1-butenyltin, butyltri-1-butenyltin, dibutyldi-3-butenyltin and butyltri-3-butenyltin using the well-known Grignard reaction. The appropriate Grignard reagent is prepared from approximately 10 g of 1-bromo-1-butene or 4-bromo-1-butene in 10 mL anhydrous tetrahydrofuran and an excess of magnesium chips.

$$RBr + Mg \rightarrow RMgBr$$

where R=butenyl group. The Grignard reagent is decanted from the excess magnesium chips, then cooled to 0° C. A stoichiometric amount of dibutyltin dichloride or butyltin trichloride in 10 mL of hexane is added dropwise to the stirred solution. The mixture is refluxed for four hours.

$$2RMgBr + Bu_2SnCl_2 \rightarrow Bu_2R_2Sn$$

or $$3RMgBr + BuSnCl_3 \rightarrow BuR_3Sn$$

where Bu=butyl group and R=1- or 3-butenyl group.

Then, the reaction mixture is cooled to 0° C. and hydrolyzed with 3% HCl to destroy excess Grignard reagent. The solvent and low boiling side products next are removed under vacuum at room temperature from the separated organic layer, and the residue is placed at the top of a 40×2 cm glass chromatography column that is slurry packed with Florisil in hexane. The tetrabutyl/butenyltins are eluted with 200 ml of hexane. Elution with hexane/ethylacetate (4:1 by volume) recovered any tributyl/butenyltin halides which may have formed. The solvents are again removed, under vacuum, from each fraction.

The product recovered in the hexane fraction is suspended in about 50 mL methanol and cooled to 0° C. in an ice bath. A stoichiometric amount of bromine in 50 mL methanol is added dropwise in dim light to the stirred tetrabutyl/butenyltin suspension. Since bromine preferentially removes the alkenyl group, four distinct products can be formed: dibutyl-1-butenyltin bromide, butyldi-1-butenyltin bromide, dibutyl-3-butenyltin bromide, and butyldi-3-butenyltin bromide.

Upon completion of the reaction, the solvent and low boiling side products are removed under vacuum at room temperature. Then, the crude product is washed through a Florisil column first with hexane to recover any unreacted tetrabutyl/butenyltin and then with 1:4 (v/v) ethyl acetate/hexane to selectively elute the tributyl/butenyltin bromide compounds. Solvent is then removed under vacuum.

Organotin copolymers are synthesized for marine anti-fouling coatings. Butenyltin copolymers for use as marine anti-fouling coatings are prepared by modifying the procedures delineated by Houghton et al., 1988 Synthesis and Characterization of Controlled Release Organotin Containing Polymers, David Taylor Research Center/SME-87/94, appended hereto as Appendix A. The changes disclosed below to the procedure of Appendix A are performed to accommodate the small amounts of polymer being prepared and the properties of the organotin compound being bound into the polymer.

First, the tributyl/butenyltin halides are dissolved in hexane and shaken 10 min in a separatory funnel with an excess of 0.1N NaOH to form the organotin oxide according to the following reactions, $$RBu_2SnBr + NaOH \rightarrow RBu_2SnOSnRBu_2$$

or $$R_2BuSnBr + NaOH \rightarrow R_2BuSnOSnR_2Bu.$$

where R=1-butenyl or 3-butenyl and Bu=butyl.

Then, the hexane layer is dried by filtration through anhydrous NaSO4. A stoichiometric amount of methacrylic acid is added and the solution is refluxed for ~3 hr. The solvent is dried by filtration through anhydrous NaSO4 and removed under vacuum at room temperature. Thus, the methacrylic acid ester of the organotin compound is formed, $$RBu_2SnOSnRBu_2 + 2 = C(CH_3)COOH \rightarrow 2\ CH_2 = C(CH_3)COOSnRBu_2$$

or $$R_2BuSnOSnR_2Bu + 2\ CH_2 = C(CH_3)COOH \rightarrow 2\ CH_2 = C(CH_3)\ COOSnR_2Bu.$$

The dry, solvent-free methacrylic acid ester of the organotin compound is then mixed with an equimolar amount of methylmethacrylate. The final proportions of monomers (total), 2-butanone and methanol preferably are 10:1.6: 14.3, respectively.

Next, one mole percent, relative to the total monomers, of the initiator, 2,2-azobis-2-methylpropionitrile, is dissolved in the 2-butanone. These reactants are mixed together and heated under reflux at 65° C. for approximately three hours by which time a thick, random 50:50 copolymer forms. The solvent is left in the copolymer for application to a surface.

Thus, in accordance with the present invention, a triorganotin ester (i.e., a triorganotin group bonded to a carboxyl acid group via an ester linkage) of an alkenylcarboxylic acid (e.g., an alkene group bonded to a carboxylic acid group) which is biocidal is formed. The triorganotin ester has the formula [H_2C=C(CH_3)C(O)O—]SnR1R2R3, wherein R1, R2 and R3 are organic groups each containing from two (2) to ten (10), and preferably four (4), carbon atoms. Stated differently, a triorganotin-containing polymer (i.e., a plurality of covalently-linked monomers containing triorganotin groups) is formed which is biocidal.

A 50:50 random copolymer of methylmethacrylate and methacrylic acid is selected as the coating matrix because this polymer, chemically bonded to tributyltin, comprises the bulk of OMP-2, one of the more successful organometallic copolymers for use as antifouling coatings. Preferably, the ester of the butenyltin species and methacrylic acid is prepared before polymerization with methylmethacrylate to attain a usable polymer. Alternatively, the triorganotin compounds can be grafted to an existing polymer or copolymer backbone that contains free carboxylic acid groups.

The properties of the final polymers, experimental and controls, are shown below in Table 1.

TABLE 1

PROPERTIES OF METHYLMETHACRYLATE (MMA)/METHYLACRYLIC ACID (MAA) COPOLYMERS

| I<br>Double Bond Position | II<br>Unsatur. Chains | III<br>Solubility | IV<br>Comments |
|---|---|---|---|
| C-1 | 1 | Dispersion | Opaque, Fragile |
| C-1 | 2 | Insoluble | Granular |
| C-3 | 1 | Soluble | Clear, Hard |
| C-3 | 2 | Soluble | Translucent, Hard |

The position of the double bond in the tin compound is indicated in column I; the number of chains that contain that double bond in shown in column II. Column III indicates the solubility characteristics of the formed polymer in the preparation solvent. Column IV shows the condition of the formed polymer upon spreading and drying.

As can be appreciated from the table above, for marine antifouling coating applications, MMA/MAA copolymers formed from dibutyl-3-butenyltin bromide and butyldi-3-butenyltin bromide are preferred. Additionally, the copolymer containing a 1-butenyl chain (i.e., the dibutyl-1-butenyltin bromide) is a sticky lump that forms a dispersion in the solvent, is not a true solution, but which nevertheless dries to a white film that may yet be amenable if coated on an appropriate substrate. Indeed, tests show that this polymer adheres to an undercoat of epoxy primer.

Thus, in accordance with the disclosure above and as indicated by FIG. 1, an antifoulant (i.e., biocidal) agent is disclosed which hydrolyzes from a polymer backbone for biocidal purposes. The surface has 12 areas which are each coated with 50:50 MMA/MAA copolymers that contain either a particular biocide or no biocide for control. On the left side area designated A, the biocide is dibutyl-3-butenyltin, B-31 (one unsaturated chain with double bond at C-3); area B has no biocide, CoP; area C has dibutyl-1butenyltin, B-11 (one double bonded chain at C-1); area D has tributyltin, B-00 (fully saturated chains); area E is 50:50 copolymer of methylmethacrylate:methacrylic acid coated with a copolymer containing dibutyl-1-butenyltin, CoP/B-11; and area F is coated with butyl-3-butenyltin, B-32 (two unsaturated chains with double bond at C-3). On the right side areas, area G has dibutyl-1-butenyltin, B-11 (one double bonded chain at C-1); area H has tributyltin, B-00 (fully saturated chains); area I is 50:50 copolymer of methylmethacrylate:methacrylic acid coated with a copolymer containing dibutyl-1-butenyltin, CoP/B-11; area J has no biocide, CoP; area K has dibutyl-3-butenyltin, B-31 (one unsaturated chain with double bond at C-3); and area L has butyl-3butenyltin, B-32 (two unsaturated chains with double bond at C-3). It is clear from the figure that the triorganotin B-00, dibutyl-3-butenyltin B-31 and butyl-3-butenyltin, B-32 inhibit marine growth while the others do not appreciably do so. Further, as indicated by FIG. 2, the antifoulant agent disclosed herein rapidly degrades for environmental compatibility. The data shown in the graph of FIG. 2 depicts what occurs after as little as 15 minutes of exposure of the copolymers (painted on a surface) to seawater. For tributyltin (B-00) the released substance is the very toxic $R_3Sn$, which degrades to less toxic compounds very slowly (half life approximately 2 weeks); therefore, most of the $R_3Sn$ is still present in the seawater after 15 minutes. For the triorganotin compounds B-31 and B-32, the released $R_3Sn$ degrades quickly; therefore, only small amounts of $R_3Sn$ and, mostly, the much less toxic $R_2Sn$ and $RSn$ can be found in the seawater after only 15 minutes.

The present invention further envisions varying the above-disclosed proportions of methylmethacrylate and organotin methacrylate to optimize the antifouling efficacy of the coating.

While the above-described triorganotin compound is fully capable of achieving the above-stated objects of the invention, it is to be understood that it is the presently preferred embodiment, that other embodiments may exist as may become obvious to those skilled in the art, that the above-described embodiment accordingly is but one representative embodiment of the present invention, and that the scope of the present invention is consequently to be limited by nothing other than the appended claims.

We claim:

1. A method for preventing the attachment of organisms to a surface which comprises administering an effective amount of a toxic substance onto the surface, wherein the toxic substance is selected from the group consisting of dibutyl-1-butenyltin, butyldi-1-butenyltin, dibutyl-3-butenyltin, and butyldi-3-butenyltin.

2. The method of claim 1, further comprising the step of disposing the substance in a polymer matrix.

3. A method for inhibiting the growth of organisms on a surface comprising administering to the surface an effective amount of a substance toxic to the organisms, said toxic substance comprising an ester having a triorganotin moiety rapidly degradable to a nontoxic specie, said triorganotin moiety having three carbon chains, each containing from two to ten carbon atoms, and having unsaturation at C-1 or C-3 on one or two of said three carbon chains to achieve rapid degradation of said toxic substance.

4. The method for inhibiting the growth of organisms on a surface comprising, administering to the surface an effective amount of a substance toxic to the organisms, said toxic substance comprising a triorganotin moiety, said triorganotin moiety having at least one site of unsaturation on one or two of its organic groups, wherein the triorganotin moiety is covalently bonded to an organic polymer.

5. The method of claim 3, wherein the triorganotin moiety is mixed into to an organic polymer.

6. The method of claim 4, wherein the organic polymer is a copolymer of methacrylic acid and methylmethacrylate.

7. The method for inhibiting the growth of organisms on a surface comprising administering to the surface an effective amount of a substance toxic to the organisms, said toxic substance comprising a triorganotin moiety, said triorganotin moiety having at least one site of unsaturation on one or two of its organic groups, wherein the triorganotin moiety is mixed into an organic polymer and wherein the organic polymer is a copolymer of methacrylic acid and methylmethacrylate.

8. A triorganotin ester of an alkenylcarboxylic acid, wherein said ester has a triorganotin moiety having three organic groups, wherein one or two of said three organic groups is an alkenyl group.

9. The triorganotin ester of claim 8 having the formula $[H_2C=C(CH_3)C(O)O-]SnR_1R_2R_3$, wherein $R_1$, $R_2$ and $R_3$ are said three organic groups each containing from 2 to 10 carbon atoms.

10. The triorganotin ester of claim 9, wherein the organic groups R1, R2 and R3 each contain four (4) carbon atoms.

11. A triorganotin ester having the formula $[H_2C=C(CH_3)C(O)O-]SnR1R2R3$, wherein R1, R2 and R3 are organic groups each containing from 2 to 10 carbon atoms of an alkenylcarboxylic acid, wherein the triorganotin group of the ester has a double bond in one or two of its organic groups, wherein the organic groups R1, R2 and R3 each contain four (4) carbon atoms and, wherein the triorganotin group is selected from the group of dibutyl-1-butenyltin, butyl-di-1-butenyltin, dibutyl-3-butenyltin, and butyldi-3-butenyltin.

12. A triorganotin polymer having a plurality of triorganotin groups covalently bonded to an organic polymer backbone, wherein each of the triorganotin groups has a double bond in one or two of its organic groups.

13. The triorganotin polymer of claim 12, wherein the polymer backbone comprises a random copolymer of methacrylic acid and methylmethacrylate.

14. A method of forming a triorganotin polymer having biocidal activity comprising:
reacting a bis(triorganotin)oxide compound with an alkenylcarboxylic acid to form a triorganotin-alkenylcarboxylate monomer and
polymerizing the monomer to form the triorganotin polymer.

15. The method of claim 14, wherein said triorganotin polymer has a plurality of triorganotin groups covalently bonded to an organic polymer backbone and each triorganotin group has at least one double bond in one or two of its organic chains.

16. The method of claim 15, wherein said organic polymer backbone includes an alkenylcarboxylic acid of methacrylic acid.

17. The method of claim 16, wherein said polymerizing is conducted in the presence of a second monomer.

18. A method of forming a triorganotin polymer having biocidal activity comprising:
reacting a bis(triorganotin)oxide compound with an alkenylcarboxylic acid to form a triorganotin-alkenylcarboxylate monomer and
polymerizing the monomer to form the triorganotin polymer, said triorganotin polymer has a plurality of triorganotin groups covalently bonded to an organic polymer backbone and each triorganotin group has at least one double bond in one or two of its organic chains, said organic polymer backbone includes an alkenylcarboxylic acid of methacrylic acid said polymerizing is conducted in the presence of a second monomer and said second monomer is methylmethacrylate.

19. A method of forming a triorganotin polymer having biocidal activity comprising:
preparing a polymeric or copolymeric backbone that contains free carboxylic acid groups and
bonding said triorganotin polymer onto said free carboxylic acid groups via an ester bond.

20. A method of forming a triorganotin polymer having biocidal activity and rapidly degrading to non-toxic species comprising:
preparing a polymeric or copolymeric backbone that contains free carboxylic acid groups and
bonding said free carboxylic acid groups via an ester bond to triorganotin groups having one or two carbon chains containing a double bond.

* * * * *